United States Patent [19]
Organ

[11] Patent Number: 6,122,544
[45] Date of Patent: Sep. 19, 2000

[54] ELECTRICAL IMPEDANCE METHOD AND APPARATUS FOR DETECTING AND DIAGNOSING DISEASES

[76] Inventor: Leslie William Organ, 1837 Kempton Rd., Charleston, S.C. 29412

[21] Appl. No.: 09/301,355

[22] Filed: Apr. 29, 1999

Related U.S. Application Data

[60] Provisional application No. 60/083,739, May 1, 1998.

[51] Int. Cl.[7] .................................................. A61B 5/053
[52] U.S. Cl. ............................................................ 600/547
[58] Field of Search ............................................. 600/547

[56] References Cited

U.S. PATENT DOCUMENTS

| | | |
|---|---|---|
| 4,291,708 | 9/1981 | Frei et al. . |
| 4,407,300 | 10/1983 | Davis ...................................... 600/547 |
| 4,458,694 | 7/1984 | Sollish et al. . |
| 4,486,835 | 12/1984 | Bai et al. . |
| 4,537,203 | 8/1985 | Machida . |
| 4,539,640 | 9/1985 | Fry et al. . |
| 4,557,271 | 12/1985 | Stoller et al. ............................ 600/547 |
| 4,583,549 | 4/1986 | Manoli . |
| 4,617,939 | 10/1986 | Brown et al. . |
| 4,688,580 | 8/1987 | Ko et al. .................................. 600/547 |
| 4,763,660 | 8/1988 | Kroll et al. . |
| 4,942,880 | 7/1990 | Slovak .................................... 600/547 |
| 5,143,079 | 9/1992 | Frei et al. . |
| 5,311,878 | 5/1994 | Brown et al. . |
| 5,465,730 | 11/1995 | Zadehoochak et al. . |
| 5,544,662 | 8/1996 | Saulnier et al. . |
| 5,588,429 | 12/1996 | Isaacson et al. ........................ 600/547 |
| 5,746,214 | 5/1998 | Brown et al. ........................... 600/547 |
| 5,807,251 | 9/1998 | Wang et al. ............................ 600/407 |
| 5,810,742 | 9/1998 | Pearlman . |
| 5,919,142 | 7/1999 | Boone et al. ........................... 600/547 |

FOREIGN PATENT DOCUMENTS 2486386  1/1982  France .

OTHER PUBLICATIONS

Pethig, R., and D.B. Kell. The Passive Electrical of Biological Systems: Their Significance in Physiology, Biophysics and Biotechnology. *Phys. Med. Biol.* 32:933–970, 1987.

Chaudhary, S.S., R.KI. Mishra, A. Swarup, and J.M. Thomas. Dielectric Properties of Normal & Malignant Human Breast Tissues at Radiowave and Microwave Frequencies. *Indian J. Biochem. Biophys.* 21:76–79, 1984.

Surowiec, A.J., S.S. Stuchly, J.R. Barr, and A. Swarup. Dielectric Properties of Breast Carcinoma and the Surrounding Tissues. *IEEE Trans. Biomed. Engng.* 35:257–263, 1988.

Jossinet, J., C. Fourcade, and M. Schmitt. A Study for Breast Imaging with a Circular Array of Impedance Electrodes. *Proc. Vth Int. Conf. Bioelectrical Impedance*, 1981, Tokyo, Japan, 83–86.

Jossinet, J.C., and E. Mbock–Mbock. Technical Implementation and Evaluation of a Bioelectrical Breast Scanner. *Proc. 10th Int. Conf. IEEE Engng. Med. Biol.*, 1988, New Orleans, USA (Imped. Imaging II).

Skidmore, R., J.M. Evans, D. Jenkins, and P.N.T. Wells. A Data Collection System for Gathering Electrical Impedance Measurements from the Human Breast. *Clin. Phys. Physio. Meas.* 8:99–102, 1987.

Piperno, G., E.H. Frei, and M. Moshitzky. Breast Cancer Screening by Impedance Measurements. *Front. Med. Biol. Engng.* 2:111–117, 1990.

Man, B., B.D. Sollish, M. Moshitzky, Y. Choukron, and E.H. Frei. Results of Preclinical Tests for Breast Cancer Detection by Dielectric Measurements. *XII Int. Conf. Med. Biol. Engng.* 1979, Jerusalem, Israel. Springer Int., Berlin, 1980, 30.4.

Sollish, B.D., E.H. Frei, E. Hammerman, S.B. Lang and M. Moshitzky. Microprocessor–assisted Screening Techniques. *Isr. J. Med. Sci.* 17:859–864, 1981.

*Primary Examiner*—John A. Jeffery
*Attorney, Agent, or Firm*—Paul Devinsky; McDermott, Will & Emery

[57] ABSTRACT

A method and apparatus for screening, sensing, or diagnosing disease states by obtaining a plurality of electrical impedance data measurements in organized patterns from two anatomically homologous body regions, one of which may be affected by disease. One subset of the data so obtained is processed and analyzed after structuring the data values as elements of an n×n impedance matrix, and deriving from these matrices their eigenvalues and eigenvectors. The matrices and their derivatives are then related by their characteristics to normal or disease states.

19 Claims, 4 Drawing Sheets

ELECTRICAL IMPEDANCE METHOD AND APPARATUS FOR DETECTING AND DIAGNOSING DISEASES

REFERENCE TO PRIOR APPLICATION

This application claims the benefit of U.S. provisional application Ser. No. 60/083,739 filed May 1, 1998 entitled "Electrical Impedance Method and Apparatus for Detecting and Diagnosing Diseases".

FIELD OF THE INVENTION

The present invention relates to a method and apparatus for detecting or diagnosing disease states in a living organism by using a plurality of electrical impedance measurements.

BACKGROUND OF THE INVENTION

Methods for screening and diagnosing diseased states within the body are based on sensing a physical characteristic or physiological attribute of body tissue, then distinguishing normal from abnormal states from changes in the characteristic or attribute. For example, X-ray techniques measure tissue physical density, ultrasound measures acoustic density, and thermal sensing techniques measure differences in tissue heat. Another measurable property of tissue is its electrical impedance, i.e. the resistance tissue offers to the flow of electrical current through it. Values of electrical impedance of various body tissues are well known through studies on intact humans or from excised tissue made available following therapeutic surgical procedures. In addition, it is well documented that a decrease in electrical impedance occurs in tissue as it undergoes cancerous changes. This finding is consistent over many animal species and tissue types, as summarized by Pethig and Kell[1]. Human breast cancers, in particular, have shown similar changes in studies such as those of Chaudhary et al.[2] and Surowiec et al.[3] Both groups examined surgically excised normal and malignant human breast tissue and obtained similar results, i.e. on average, the electrical impedance of breast cancer tissue was about one-third that of the normal surrounding breast tissue.

Electrical impedance imaging has been proposed to create a picture of electrical impedance differences within a body region[4,5,6] much as an X-ray provides a picture of differences in physical density. One of the incentives to do so is the potential application of electrical impedance imaging as a screening technique for breast cancer, either as a replacement of or supplement to X-ray mammography. Mammography has reasonable sensitivity for detecting abnormalities when present, but the technique fails to detect about 5 to 15% of breast cancers. This is due to several factors, including concealment of the cancer by overlying normal, but dense, breast tissue, failure of mammography to image certain portions of the breast, as well as errors in perception. Mammography has relatively low success for distinguishing malignancies from other abnormalities, and of the approximately 500,000 breast biopsies performed in the United States each year because of an abnormality detected on mammography, only 15 to 30% of the biopsies reveal cancer. This lack of specificity not only results in needless anxiety and an unnecessary procedure, but adds a significant cost to the breast cancer screening program.

There have been a number of reports of attempts to detect breast tumors using electrical impedance imaging.[4,5,6,7,8,9,10] However, there are basic problems when trying to construct an image from impedance data. The paths through tissue of X-rays are straight lines. In contrast, electrical current does not proceed in straight lines or in a single plane; it follows the path of least resistance, which is inevitably irregular and three dimensional. As a result, the mathematics for constructing the impedance image is very complex and requires simplifying assumptions that greatly decrease image fidelity and resolution. Not surprisingly, in view of the image reconstruction difficulties, either no clinical data were published in any of these reports, or if they were, the images were of low resolution and difficult to interpret.

BRIEF SUMMARY OF THE INVENTION

The present invention does not attempt to create an image of a cancer and surrounding tissue. A cancer need not be "seen" to be detected; its presence can be detected by a marker associated with it, in this case a change in its electrical impedance, and a technique such as the present invention sensitive to the marker. In this manner, complexity of underlying structure is not important, and a previously unachievable task becomes greatly simplified and consequently possible. Although the present invention can be applied to any two homologous body regions, the application to be discussed scans for the presence or absence of breast abnormalities, particularly benign and malignant tumors. While not intending to be bound by any particular theory, the method of the invention may arise from the following assumptions and hypotheses:

1. The tumor will occur in only one breast.
2. Both breasts are structurally similar, and therefore can be expected to be approximate mirror images (homologous) with respect to their impedance characteristics.
3. If impedance measurements are taken in a multiplicity of directions or paths across the breast (I call this an impedance scan), the presence of tumors, which are known to have a significantly lower impedance than the normal tissue they replace, will distort or change the impedance in at least some of the paths of current flow.
4. The magnitude of decreased impedance is greater for malignant tumors than for benign ones, providing a method for differentiating between these tumor types.
5. There will always be some differences in impedance between breasts in the normal individual; but these differences will be less than the differences when a cancer is present.

In one embodiment of the invention, data are obtained in organized patterns from two anatomically homologous body regions, one of which may be affected by disease. One subset of the data so obtained is processed and analyzed by structuring the data values as elements of an n×n impedance matrix. The matrices can be further characterized by their eigenvalues and eigenvectors. These matrices and/or their eigenvalues and eigenvectors can be subjected to a pattern recognition process to match for known normal or disease matrix or eigenvalue and eigenvector patterns. The matrices and/or their eigenvalues and eigenvectors derived from each homologous body region can also be compared, respectively, to each other using various analytical methods and then subjected to criteria established for differentiating normal from diseased states.

In another embodiment of the invention, a not entirely exclusive subset of homologous impedance differences from homologous body regions are compared in various manners, and the resultant differences used as an indicator of disease states. These impedance differences can also be represented as color-coded lines plotted in a pictorial representation of the two homologous body regions. The color codes indicate magnitude of impedance difference. These plots can provide a visual indication of certain disease states and their location. The use of impedance differences in the present invention "subtracts out" an otherwise complex and voluminous amount of impedance data produced by most current paths that, while irregular and three dimensional, are nevertheless substantially impedance-identical because the paths were virtually identical in both breasts. The differences that remain are much more manageable analytically, and can be used to identify disease states.

An important aspect of the invention is the electrode array, designed and fabricated so that electrode position and spacing are, as closely as possible, identical in the two breasts in order not to introduce artifactual differences related to the array itself. Another aspect of the invention that contributes to the simplicity and reliability of the impedance scanning method is the design and implementation of the apparatus for acquiring, displaying, and analyzing the data.

Whereas the illustrated example of the present invention is a novel and improved method and apparatus for detecting and locating breast cancers, the invention can also be applied to other diseases or conditions in which there is a distinguishable difference in electrical impedance in the tissue as a result of the disease or condition. For example, the occurrence of a deep venous thrombosis in the thigh or leg would cause a change in the circulatory dynamics which would be reflected by a change in the electrical impedance of the affected region.

A further objective of the present invention is to provide a novel and improved method and apparatus for detecting and locating diseases or conditions in any region of the body in which the electrical impedance of the region containing the disease or condition can be compared to an essentially identical, normal body region; for example, right and left forearms, right and left thighs, or right and left calves.

A still further objective of the present invention is to provide a novel and improved method and apparatus for detecting and locating diseases or conditions in any region of the body in which the electrical impedance of the region containing the disease or condition can be compared to another normal body region that, while not entirely identical, is consistently and constantly different; for example, right and left sides of the abdomen. (In other words, the differences between the two regions being compared is a known constant in a healthy person and therefore can be subtracted out when performing a comparison.)

DETAILED DESCRIPTION OF THE INVENTION

Electrical Impedance and the Four Electrode Measurement Technique.

Figure 1:
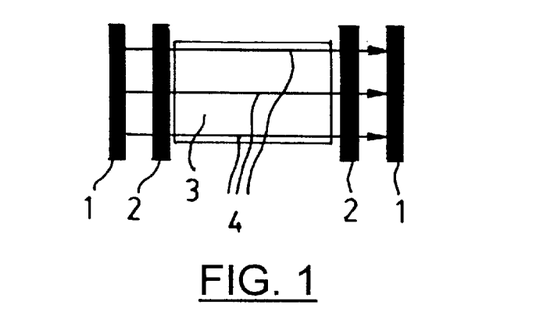
FIG. 1 is an illustration of the four electrode impedance measurement technique.

Electrical impedance is most accurately measured by using four electrodes as shown in FIG. 1. The outer pair of electrodes 1 is used for the application of current 1, and the inner pair of electrodes 2 is used to measure the voltage V that is produced across the tissue (or generally, material) 3 by the current. The current 1 flowing between electrodes 1 is indicated by the arrows 4. The impedance Z is the ratio of V to I; i.e., Z=V/I. It is well known that using separate electrode pairs for current injection and voltage measurement produces a more accurate measurement of impedance because polarization effects at the voltage measurement electrodes are minimized.

Impedance consists of two components, resistance and capacitive reactance (or equivalently, the magnitude of impedance and its phase angle). Both components are measured, displayed, and analyzed in the present invention. However, for the purpose of explanation of the invention, only resistance will be used and will interchangeably be referred to as either resistance or the more general term impedance.

The Breast Electrode Array

Figure 2:
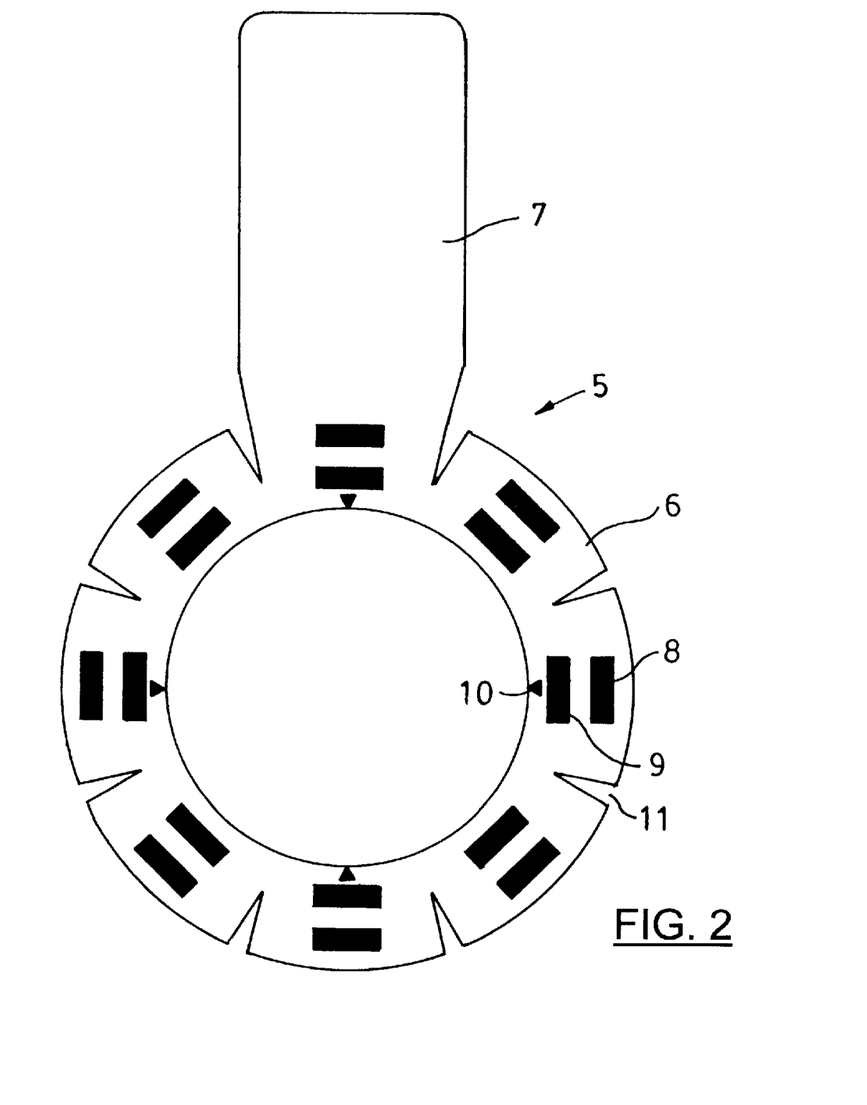
FIG. 2 is an illustration of a breast electrode array of the invention.

FIG. 2 discloses a breast electrode array 5 of the invention that has eight electrode pairs, each pair consisting of an outer electrode 8 for current injection and an inner electrode 9 for voltage measurement. The illustrated implementation of the array has a main section 6 and a tail section 7. Eight pairs of rectangular electrodes in circular orientation are shown, but there are many alternatives that could be advantageously used with the present invention: more electrode pairs; different electrode shapes; other shapes for the main body and tail sections of the array; and other geometrical arrangements of the electrodes, e.g. radial sectors with three or more electrodes. Regardless of the electrode arrangement, four electrodes must be used for each impedance measurement, two outer electrodes between which current is injected, and two inner electrodes at which voltage is measured. The electrodes are attached to the skin side of the main section 6 of the array 5 and are made of an electrically conductive, self-adhesive material so that when the array is positioned on the skin and pressed against it, the adhesive quality of the electrodes assures good skin fixation. Alternatively, additional adhesive material can be used at various positions on the main section 6 and/or the tail section 7 of the array. In order to assure impedance is measured in all regions of the breast, electrode arrays 5 are made in different sizes for use in women with different breast cup sizes.

Figure 3A:
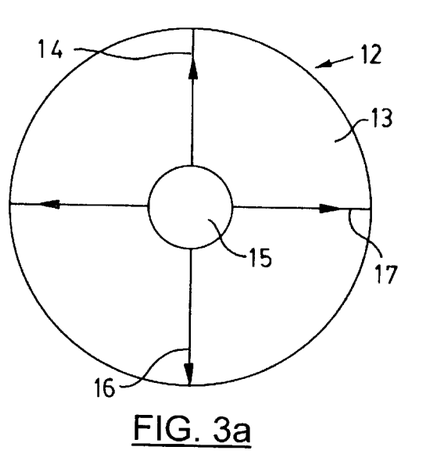
FIG. 3A is an illustration of a positioning template for the breast electrode array of FIG. 2.
Figure 3B:
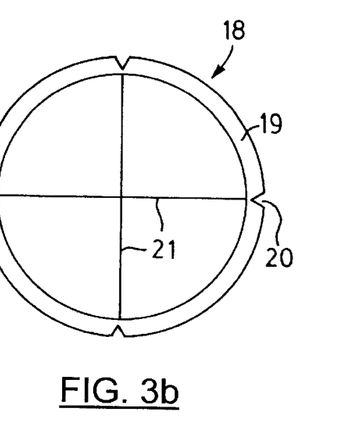
FIG. 3B is an illustration of a positioning ring for the breast electrode array of FIG. 2.

For clarity of description, lead connections for the electrodes are not shown in FIG. 2. The material used for the main section 6 of the array 5, and to a lesser degree for tail section 7, may be flexible to allow the array to conform to the shape of the breast. (Such material may for example be a suitable fabric, or an appropriate plastic such as flexible vinyl sheet material.) Shape conformity is further aided by cutouts or darts 11 that allow the material to overlap and thereby prevent it from crumpling and possibly lifting part or all of an electrode off the skin. More accurate and consistently identical positioning of electrode arrays on both breasts is aided by the index marks 10 shown at four locations on the inner edge of the main section 6. Before applying an array to the skin surface of the breast, a transparent, flexible positioning template 12, shown in FIG. 3A, is positioned on the breast with central cutout 15 centered about the nipple and the template rotated so that crosshair line 16 is aligned with the body's vertical axis and crosshair 17 is aligned with the body's transverse (horizontal) axis. An ink or other mark is made on the skin surface through the cutouts 14 of the positioning template 12. The template is then removed and the electrode array is applied with its index marks 10 shown in FIG. 2 aligned with the ink marks on the skin. An alternative embodiment of a device for positioning the breast electrode array, an array positioning ring 18, is shown in FIG. 3B. It consists of a ring 19 that has an outer diameter equal to the distance between the tips of diametrically opposed index marks 10 of FIG. 2. The ring 19 of FIG. 3B has four notches 20 corresponding to each of the index marks 10 of FIG. 2. Fine crosshairs 21 extend from the inner side of ring 19 between diametrically opposed notches, with the central junction of the crosshairs serving to center the array positioning ring 18 over the nipple.

Figure 4:
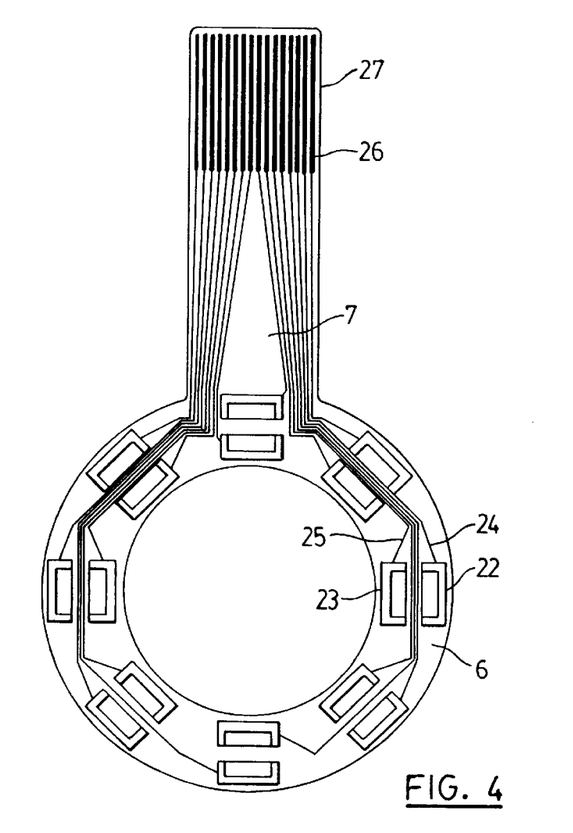
FIG. 4 shows an implementation of lead wiring for the breast electrode array of FIG. 2.

FIG. 4 shows an implementation of electrode lead wiring for the breast electrode array. Electrically conductive material is deposited or otherwise applied to both surfaces of the main section 6 (the darts 11 are not shown in this drawing) and the tail section 7 of the array as follows:

on the skin side of main section 6 the conductive material has the form of "U" shaped electrode connection areas 22 and 23 for outer and inner ring electrodes respectively which are attached in position over these connection areas. Many other shapes could be used for the connection areas, the primary consideration being a large enough area to ensure low resistance electrical continuity with the skin electrodes. Fine, conductive pathways (or leads) 24 and 25 are applied to the non-skin side of main section 6 and tail section 7. The flexible material from which the main and tail sections are fabricated is nonconductive, and so insulates conductive pathways 24 and 25 from electrode connection areas 22 and 23. At one end each lead 24 and 25 penetrates through main section 6 and is soldered to (or otherwise electrically attached to) the electrode connection areas 22 and 23 respectively. At their other end the leads bunch in the tail section 7 to make individual electrical contact with conductive fingers 26 to form a ribbon type connector 27.

Alternative embodiments of electrode arrays are possible that would not necessitate the attachment of adhesive electrodes to the subject's skin. For example, the subject could lay prone on a table with an opening for the breasts to fall freely downward. A flat plate, or cone, or other shaped holder with an array of electrodes on its upper surface, could then be moved upward, guided by landmarks on the breast and/or chest wall, to compress the breast to the extent required for good electrode contact. Further compression may serve beneficially to bring a tumor closer to the electrodes, or create a breast shape more conducive to analysis. A variant of this method would position the subject between 0 and 90°, say at 45° to the horizontal, again allowing the breasts to fall through an opening with, in this embodiment, a shelf at a suitable angle, say 45°, to guide the breasts. Another variant of this method would have the subject erect, as in conventional X-ray mammography, and use, for example, mediolateral oblique and craniocaudal compression, as in conventional X-ray mammography procedure, but with electrode arrays in the compression plates.

Acquiring Impedance Data

Figure 5:
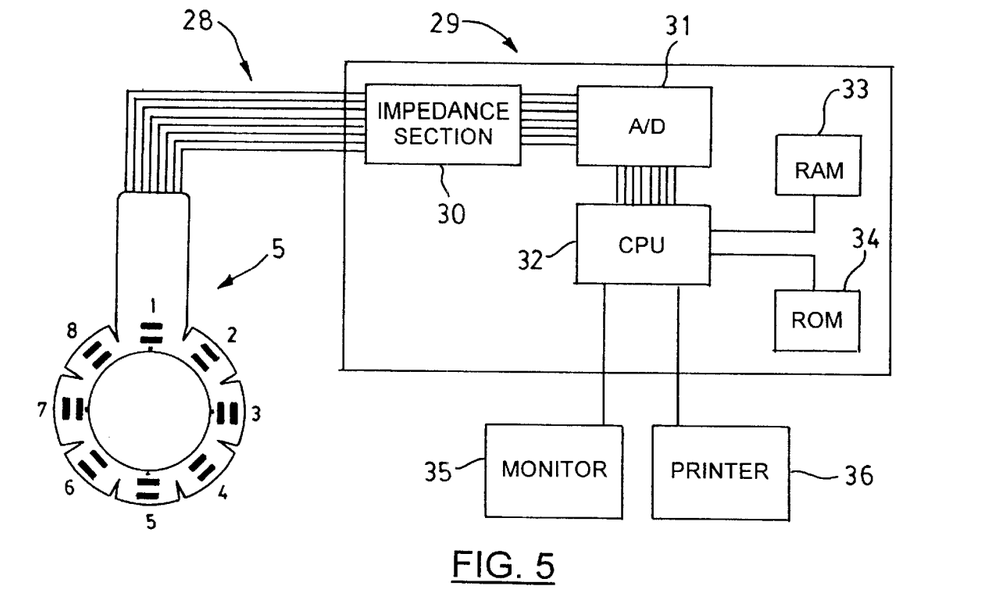
FIG. 5 is a block diagram of apparatus for performing the method of the invention.

FIG. 5 discloses a basic block diagram of the data acquisition and analysis apparatus 29 for automatically obtaining, processing and analyzing impedance measurements. For the purposes of illustration, the apparatus 29 will be described as employed for screening, locating and diagnosing breast cancer. However, it should be recognized that the method and apparatus of the invention can be employed in a similar manner for screening or diagnosis at other body sites and for other conditions and diseases. A breast electrode array 5 of 16 electrodes arranged as two concentric circles of eight electrodes each is shown in FIG. 5. Conventional ECG monitoring electrodes, cut down to appropriate size with the metal tab connector intact, were used. A plurality of leads 28 is intended, in this illustration, to number 16, one for each electrode. More generally, more electrodes, other electrode arrangements, and other electrode types, could be used in this application to produce more detailed and useful results. Also, the device and method of this invention contemplate the use of a variety of electrode arrays and leads, depending on other applications for which the apparatus 29 is used.

In preparation for the acquisition of impedance data, the subject lies supine on an examining table and the skin in the area the array will be placed on is gently cleansed with alcohol to debride the surface. The breast electrode array 5 is carefully oriented with respect to body axes and centered about the nipple as previously described, and then lightly pressed against the skin over each electrode to fix the array to the skin. The breast electrode array 5 as described for the present invention may not be reusable, in which case another array would be used for the second breast. It may, however, be possible to modify the design of the array to allow more than one use.

As previously described, the four electrode technique is used to measure electrical impedance. Continuous 50 kilohertz sine wave current is injected between two of the eight electrodes in the outer ring of the breast electrode array 5. Use of this frequency and waveform is standard practice for many bioimpedance applications, but there is an extended range of useable frequencies and, to a lesser degree, other waveforms. For the right breast, the electrode pairs are numbered clockwise 1 to 8, and for the left breast, electrode pair numbering is counterclockwise so that mirror-imaged electrode pairs will always be compared. The injected current, whose amplitude is low enough that it is imperceptible, creates electric field potentials (voltages) throughout the entire breast and adjacent chest wall. In particular, it creates voltages at the eight electrodes in the inner ring of the electrode array. Measuring the voltage difference between any two of the inner electrodes, and dividing it by the value of the current injected between the two outer electrodes gives, by Ohm's law, the value of the impedance. For example, if current $I_{1,3}$ is defined as being applied between the outer electrodes of electrode pairs I and 3, and voltage $V_{1,7}$ is measured between the inner electrodes of electrode pairs 1 and 7, the resultant impedance Z is $$Z = \frac{V_{1,7}}{I_{1,3}}$$

The apparatus 29 is a multichannel device that is connected to electrode leads 28 from the breast electrode array 5. A central control unit, consisting of central processing unit (CPU) 32 and RAM and ROM memories 33 and 34, selects in rapid succession, one set of four electrodes at a time, a multiplicity of sets of two outer electrodes for current injection and two inner electrodes for voltage measurement to perform what I call an impedance scan. Four electrode impedance measurement is made by the conventionally designed impedance section 30. The analog-to-digital (A/D) converter 31 is of known type, and converts the analog impedance measurement to a digitized form. Depending on the number of array electrodes, more than one A/D converter may be needed. Digital input data from the A/D converter 31 are processed by the CPU, where they undergo real time analyses for error checking, routing to the monitor 35 for display of raw or processed data, as well as storage in memory for further analysis and output to the monitor 35 and printer 36.

The total number of possible combinations of two current electrodes and two voltage electrodes is very large. However, mathematical and electrical circuit theory can show that there are only 49 such combinations that are independent and that all other combinations can be calculated from the set of 49. This set is obtained as follows: current is applied between the outer electrodes of electrode pairs 1 and 2 and then, in turn, the voltage between the inner electrode of electrode pair 1 and all other inner electrodes are measured, i.e., $V_{1,2}$, $V_{1,3}$ ... $V_{1,8}$. Dividing each of these voltages by $I_{1,2}$, the current between the outer electrodes of electrode pairs 1 and 2, gives the first seven impedance values. Current is next applied between the outer electrodes of electrode pairs 1 and 3, $I_{1,3}$, which will create a new pattern of electric field potentials. Then, the voltage is again measured between the inner electrode of electrode pair 1 and all other inner electrodes ($V_{1,2}$, $V_{1,3}$ ... $V_{1,8}$). Dividing each of the voltages by $I_{1,3}$ gives the next seven impedance values. This process is repeated for current applied between the outer electrodes of electrode pairs 1 and 4, 1 and 5, 1 and 6, 1 and 7, and 1 and 8, to produce, finally, seven sets of seven impedance values. Placing these impedance values (elements) in a 7-row by 7-column grid results in what I call the impedance matrix.

There is a special subset of 7 impedance values in the 49 element set—those that use the same pair of electrodes for current injection and voltage measurement; for example, current I1,3 applied between the outer electrodes of electrode pairs 1 and 3, and voltage $V_{1,3}$ measured between inner electrodes of the same electrode pairs gives impedance $$Z = \frac{V_{1,3}}{I_{1,3}}$$

I call impedances in this subset Zsame type impedances. They are:

$Z_{1,2}$ $Z_{1,3}$ $Z_{1,4}$ $Z_{1,5}$ $Z_{1,6}$ $Z_{1,7}$

There is additional value, as will be disclosed under Data Analysis, in measuring all possible $Z_{same}$ impedances, another 21 measurements, as listed below:

$Z_{2,3}$ $Z_{2,4}$ $Z_{2,5}$ $Z_{2,6}$ $Z_{2,7}$ $Z_{2,8}$ $Z_{3,4}$ $Z_{3,5}$ $Z_{3,6}$ $Z_{3,7}$ $Z_{3,8}$ $Z_{4,5}$ $Z_{4,6}$ $Z_{4,7}$ $Z_{4,8}$ $Z_{5,6}$ $Z_{5,7}$ $Z_{5,8}$ $Z_{6,7}$ $Z_{6,8}$ $Z_{7,8}$

Therefore, a complete set of impedance measurements for one breast, when the illustrated eight pair electrode array is used, consists of 49 measurements for the impedance matrix, and another 21 measurements to obtain all values for $Z_{same}$, resulting in a total of 70 impedance measurements for each breast. I call the organized process of selecting lead sets and obtaining these measurements an impedance scan. As the values are being acquired, their accuracy and reliability are checked in real time by a novel error detection program in the central control unit that uses algorithms based on 1) expected values of impedances related to their position in the matrix, 2) expected ratios of the resistive and reactive components of impedance, and 3) a comparison of the 21 measured $Z_{same}$ values listed above to their calculated values derived from the impedance matrix.

Data Analysis a) The Impedance Matrix of Homologous Body Regions

In the methods of this invention, the breast is considered as a non-homogeneous, electrically conducting object with M+1 electrode pairs (to be referred to in this discussion simply as an "electrode," one that can be used for both current injection and voltage measurement without electrode polarization). I assign one electrode as the reference electrode with zero potential. The current at the reference electrode is the sum of the currents that are applied to the other M electrodes. The impedance matrix Z relates the currents $I_i$, the current through the ith electrode, and the voltages $V_i$, the potential difference between the ith electrode and the reference electrode, where i=1,2,3, . . . ,M, as follows:

$$\begin{bmatrix} V_1 \\ V_2 \\ V_3 \\ \vdots \\ V_M \end{bmatrix} = Z \times \begin{bmatrix} I_1 \\ I_2 \\ I_3 \\ \vdots \\ I_M \end{bmatrix}$$

which can be condensed as V=Z×I.

For an object with M+1 electrodes as described above, the impedance matrix Z is defined as an M×M matrix:

$$Z = \begin{bmatrix} Z_{11} & Z_{12} & Z_{13} & \cdots & Z_{1M} \\ Z_{21} & Z_{22} & Z_{23} & \cdots & Z_{2M} \\ Z_{31} & Z_{32} & Z_{33} & \cdots & Z_{3M} \\ \vdots & \vdots & \vdots & \vdots & \vdots \\ Z_{M1} & Z_{M2} & Z_{M3} & \cdots & Z_{MM} \end{bmatrix}$$

Each matrix element $Z_{ij}$ (i,j=1,2,3, . . . ,M) is equal to $V_i/I_j$ when all currents except the current at the jth electrode are equal to zero. In a given subject, the impedance matrix Z is unique for a given pattern of breast electrodes and therefore represents the "signature" of the breast. Associated with certain types of matrices, including the impedance matrices as structured in the present invention, are values called eigenvalues and vectors called eigenvectors. These words are Anglo-German hybrids which use the German "eigen" for characteristic or particular. Characteristic or particular in the sense that by mathematical analysis each 7×7 impedance matrix can be represented by a set of seven numbers, i.e. seven eigenvalues, that are unique to that matrix. Furthermore, associated with each of these numbers (eigenvalues) is a unique, 7D vector, its eigenvector. Since the eigenvalues and eigenvectors characterize the matrix, and the matrix in turn is sensitive to tissue changes resulting from disease, an object of the present invention is the use of eigenvalues and eigenvectors as a means of detecting and diagnosing disease states. The number of eigenvalues and eigenvectors available for this purpose will vary with the size of the impedance matrix, increasing as the number of electrodes used in the array becomes larger.

Once available, the Z matrix (or R matrix, or Xc matrix, if Z is resolved into its resistive and capacitive reactive components) from each homologous body region can be used in the following ways in the present invention to screen for or diagnose disease:

1. Perform pattern recognition analyses on the matrix;
2. Examine the determinant, eigenvalues and eigenvectors of the matrix; and
3. Compute the joule losses for each breast by evaluating $P = I^T Z \, I^*$ where T denotes matrix transposition and * denotes complex conjugation. If P is significantly lower for one breast, it may indicate that a cancer is present in the breast with the lower P.

The methods of the present invention recognize that an impedance matrix is not an image of the structure of the underlying breast, and indeed the complexity and impracticality of attempting to construct impedance images is purposely avoided. Instead, a relatively simple new test procedure called an impedance scan is performed in an organized fashion with inventive devices to ensure accuracy and reproducibility of results in general and precise mirroring of the procedure between two sides or two regions in particular. Impedance values are obtained in a manner that allows them to be organized into an impedance matrix. These values, the elements of the matrix, depend on the electrical characteristics of the underlying structures. Any electrical change or abnormality in a structure will produce a change in the impedance matrix and its eigenvalues and eigenvectors. And if there is a (reasonably) identical normal structure or region, detection and diagnosis of the difference produced by the abnormality is greatly simplified by comparison with the normal structure and by clinical experience that has previously related the difference with the disease state that produced it.

Figure 6:
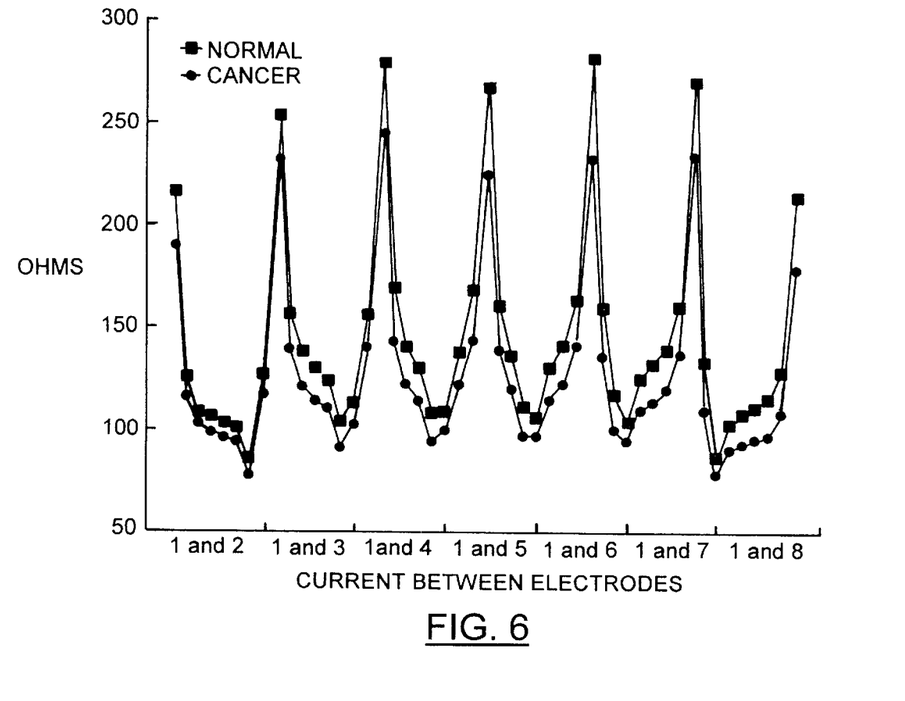
FIG. 6 is a plot of an impedance matrix, a method of the present invention, obtained from a subject with cancer in the left breast.

An example of a graphical plot of an impedance matrix (specifically, the resistive component) in a subject found to have an infiltrating ductal adenocarcinoma in her left breast is shown in FIG. 6. The x-axis indicates the selection of outer electrodes for current injection, e.g. between electrodes 1 and 2, between 1 and 3, . . . between 1 and 8. As described previously, for each such selection, seven values of impedance are obtained by measuring voltages between electrodes 1 and 2, 1 and 3, . . . 1 and 8. In the graph, these seven impedance values are shown in order proceeding from left to right for each current selection, with impedance (resistance) magnitude indicated by the y-axis height. As predicted by the known decrease in impedance of malignant tissue, the matrix plot for the breast with a cancer has lower impedances. This effect is seen throughout in this example; in other subjects, it occurred in most, but not all regions.

b) Homologous Impedance Differences over Homologous Body Regions

Another object of the method of the present invention is the use of the special set of impedance values, referred to previously as $Z_{same}$, as a means of detecting and diagnosing disease states. This set, for a 7×7 matrix, has 28 values and is shown below. Larger matrices will have correspondingly larger sets.

$$Z_{1,2} \; Z_{1,3} \; Z_{1,4} \; Z_{1,5} \; Z_{1,6} \; Z_{1,7} \; Z_{1,8}$$
$$Z_{2,3} \; Z_{2,4} \; Z_{2,5} \; Z_{2,6} \; Z_{2,7} \; Z_{2,8}$$
$$Z_{3,4} \; Z_{3,5} \; Z_{3,6} \; Z_{3,7} \; Z_{3,8}$$
$$Z_{4,5} \; Z_{4,6} \; Z_{4,7} \; Z_{4,8}$$
$$Z_{5,6} \; Z_{5,7} \; Z_{5,8}$$
$$Z_{6,7} \; Z_{6,8}$$
$$Z_{7,8}$$

$Z_{same}$ impedance measurements (and all other measurements) for normal subjects have some differences because there are always small anatomic or physiologic side-to-side differences in homologous body structures. These, however, can be expected to differ from side-to-side impedance differences when one side is affected by a disease that changes its electrical properties. One method of analysis in the present invention uses the following mathematical functions to provide a set of statistics to distinguish between impedance scans from normal subjects and those in which there is an underlying disease condition. The examples given are for an eight electrode pair array; they apply equally well for other numbers of pairs. The statistics are:

1. Mean of Algebraic Differences: The algebraic side-to-side difference between each of the 28 $Z_{same}$ impedance values is taken, and the mean algebraic difference for the 28 values is calculated.
2. Mean of Absolute Differences: The absolute side-to-side difference between each of the 28 $Z_{same}$ impedance values is taken, and the mean absolute difference for the 28 values is calculated.
3. Number of Matches: The number of matching homologous impedance chords. A related statistic, the Number of Mismatches=28−Number of Matches.
4. Mean of Algebraic Differences/Number of Mismatches.
5. Mean of Absolute Differences/Number of Mismatches.

Confidence intervals about these means are calculated based on measures such as one or two standard deviations. Some or all of these 25 statistics, and/or other ones derived from the impedance matrix, eigenvalues or eigenvectors, are used as part of a diagnostic algorithm for breast cancer screening. The mean side-to-side difference statistics generated by the impedance scan are examined (preferentially by computer) to determine whether a significant number of the means or certain subsets of means, weighted or otherwise, fall within the confidence limits of normal or cancer groups. If the determination is for the normal group, the impedance scan is normal; if the determination is for the cancer group, a breast cancer is suspected.

Another method of analysis in the present invention, which I call the bin method, uses the minimum and maximum values of the 56 $Z_{same}$ impedance values (28 per side) for a given subject to define the impedance range for that subject, then the range subdivided into eight equal smaller size ranges, or bins. Using as an example the subject in FIG. 7 (cancer in the upper inner quadrant of the right breast), it can be seen that the range of impedances varied from 75 to 218 ohms, giving eight bins of 75 to 92, 93 to 110, 111 to 128, . . . and 201 to 218 ohms. The right and left breasts are symbolized in FIG. 8 by circles, and the impedances between electrode pairs are represented as wide lines or chords. The magnitude of each impedance is indicated by the density of gray shading (or alternatively by color) with the lowest impedances (those within the 75 to 92 ohm bin) assigned black, impedances at the next level (the 93 to 110 ohm bin) are assigned dark gray, and so on until the highest impedances (the 201 to 218 ohm bin) which are assigned white. I call FIG. 7 an impedance chord plot.

Figure 7:
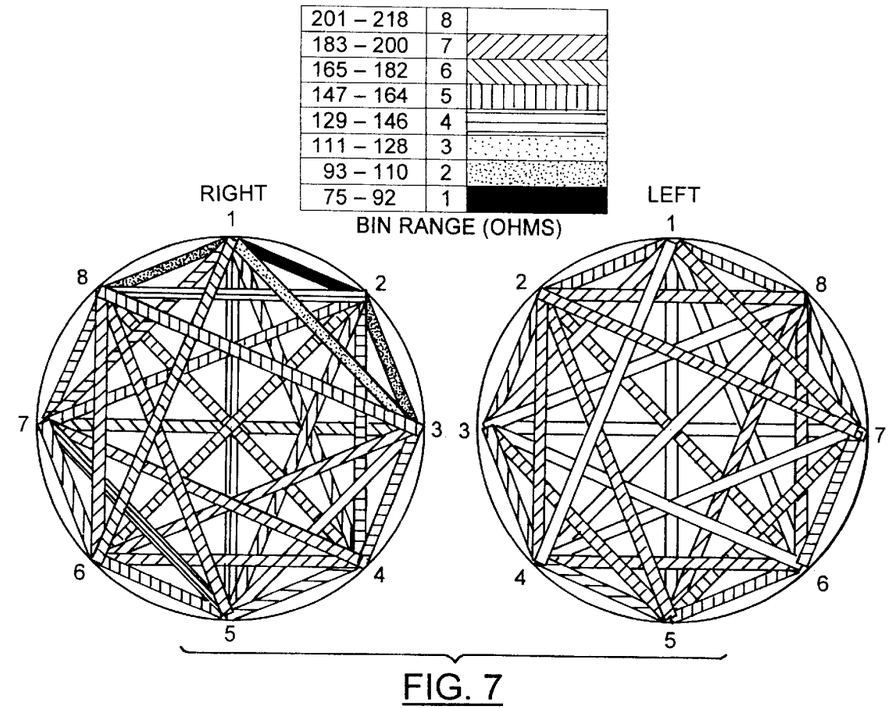
FIG. 7 is an impedance chord plot in a subject with a cancer in the upper inner quadrant of her right breast. The breasts are symbolized as circles and the 28 impedance measurements in each breast are represented by chords of the circle. Impedance values are assigned to one of eight bins and are represented by the density of shading.
Figure 8:
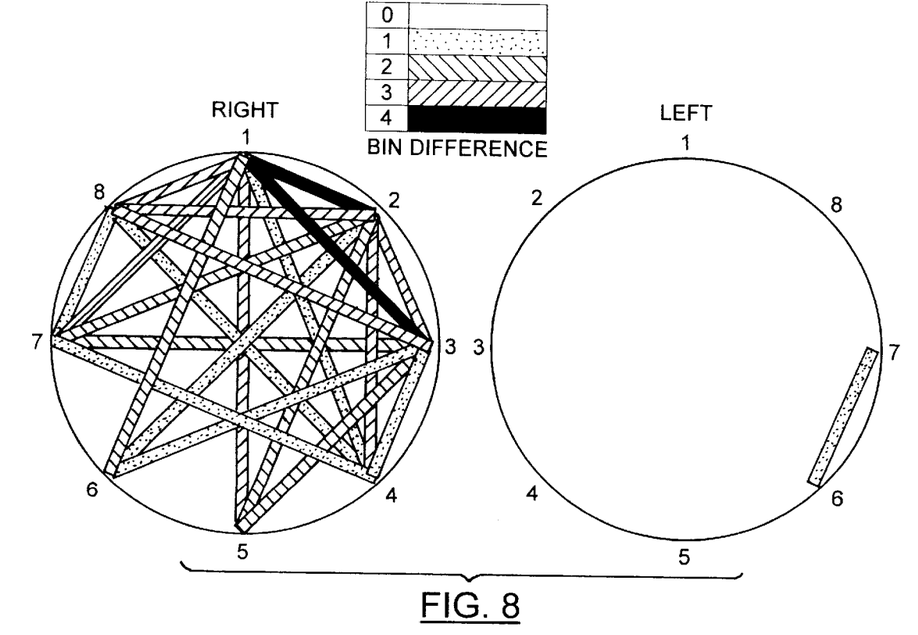
FIG. 8 is an impedance difference chord plot from the same subject in FIG. 7. The chords now represent the bin difference between each pair of the homologous 28 measurement sites.

Another type of chord plot, one that more clearly demonstrates the impedance difference between breasts, is shown in FIG. 8. The chords now represent impedance bin differences, with the chord plotted on the side of lower impedance for that site. For example, the impedance value between electrode pairs 1 and 2 on the right side fitted into bin 1 (the 75 to 92 ohm range), and the impedance value between electrode pairs 1 and 2 on the left side fitted into bin 5 (the 147 to 164 ohm range). Therefore the bin difference was 4, and a very dark gray (or dark color) chord is plotted between electrode pairs 1 and 2 on the right side. I call FIG. 8 an impedance difference chord plot. By following increasingly darker shades or colors, the eye is led to the upper inner quadrant of the right breast where the cancer was located.

Chord plots are not images of the breast; the cancer is not outlined as with an X-Ray mammogram. Rather, they provide a graphical representation of the breast, showing by impedance chords and bin difference chords the probable location of a cancer.

As previously mentioned, while the invention is particularly suited for detecting and locating breast cancers, the invention can also be applied with respect to other diseases or conditions where there are two essentially identical body regions, so that impedance measurements for each can be compared with each other and the differences can be analyzed to diagnose the possibility of a disease state in one of the parts. The disease being diagnosed may be any disease which affects the impedance of the body part in question.

In addition, as mentioned, the body parts in question may not be entirely identical, so long as the differences between them are consistent and well known in the case of a healthy living organism. In this application, the known normal impedance differences between the two parts being compared can be subtracted from the impedance set of the part having the larger impedances, or can be added to the set of impedances of the part having lower value impedances, to "normalize" the two sets of impedances, after which the differences between the respective impedance sets can be compared as before. Alternatively, the normal known differences can be removed from the impedance "difference" calculations after the impedance differences have been determined.

Further, while the invention has been described with respect to diagnosis of a disease state in a human being, the invention may also be applied, where appropriate, to an animal.

While preferred embodiments of the invention have been described, it will be appreciated that various changes may be made within the scope of the attached claims.

ENDNOTES

1. Pethig, R., and D. B. Kell. The passive electrical properties of biological systems: their significance in physiology, biophysics and biotechnology. *Phys. Med. Biol.* 32:933–970, 1987.
2. Chaudhary, S. S., R. K. Mishra, S. Swarup, and J. M. Thomas. Dielectric properties of normal and malignant breast tissues at radiowave and microwave frequencies. *Indian J. Biochem. Biophys.* 21:76–79, 1984.
3. Surowiec, A. J., S. S. Stuchly, J. R. Barr, and A. Swarup. Dielectric properties of breast carcinoma and the surrounding tissues. *IEEE Trans. Biomed. Engng.* 35:257–263, 1988.
4. Jossinet, J., C. Fourcade, and M. Schmitt. A study for breast imaging with a circular array of impedance electrodes. *Proc. Vth Int. Conf. Bioelectrical Impedance,* 1981, Tokyo, Japan, 83–86.
5. Jossinet, J. C., and E. Mbock-Mbock. Technical implementation and evaluation of a bioelectrical breast scanner. *Proc. 10th Int. Conf. IEEE Engng. Med. Biol.,* 1988, New Orleans, U.S.A. (Imped. Imaging II).
6. Skidmore, R., J. M. Evans, D. Jenkins, and P. N. T. Wells. A data collection system for gathering electrical impedance measurements from the human breast. *Clin. Phys. Physiol. Meas.* 8:99–102, 1987.
7. Morimoto, T., S. Kimura, Y. Konishi, K. Komaki, T. Uyama, Y. Monden, Y. Kinouchi, and T. Iritani. A study of the electrical bio-impedance of tumors. *J. Invest. Surg.* 6:25–32, 1993.
8. Piperno, G., E. H. Frei, and M. Moshitzky. Breast cancer screening by impedance measurements. *Front. Med. Biol. Engng.* 2:111–117, 1990.
9. Man, B., B. D. Sollish, M. Moshitzky, Y. Choukron, and E. H. Frei. Results of preclinical tests for breast cancer detection by dielectric measurements. *XII Int. Conf. Med. Biol. Engng.* 1979, Jerusalem, Israel, Springer Int., Berlin, 1980, 30.4.
10. Sollish, B. D., E. H. Frei, E. Hammerman, S. B. Lang and M. Moshitzky. Microprocessor-assisted screening techniques. *Isr. J. Med. Sci.* 17:859–864, 1981.

I claim:

1. A method of diagnosing the possibility of a disease state in one of first and second substantially similar parts of a living organism, said method comprising:
   (a) obtaining a plurality of impedance measurements across each of said parts and thereby producing first and second sets of impedance measurements, said first set for said first part, and said second set for said second part,
   (b) said measurements of said first set being taken across predetermined portions of said first part, and each measurement of said first set having a corresponding measurement in said second set taken across a corresponding portion of said second part,
   (c) comparing said sets to determine differences therebetween, and where there is a substantial difference, diagnosing the possibility of a disease state.

2. A method according to claim 1 wherein said parts of said living organism are the breasts of a person, and said disease state is a cancer.

3. A method according to claim 2 wherein said impedance measurements for each breast are taken between a plurality of pairs of points encircling each breast.

4. A method according to claim 3 wherein said measurements are taken using an electrode array having two electrodes for each point, one electrode to inject or receive electrical current, and the other electrode for measuring voltage.

5. A method according to claim 4 wherein electrical current is injected and withdrawn between successive pairs of points, and while current is being injected between each pair of points, voltage measurements are taken between the points of such pairs and also between a plurality of pairs of other points of said electrode array.

6. A method according to claim 5 wherein impedance values are determined from said respective pairs of points and said method comprising arranging said values in a mathematical matrix and performing matrix analysis for said diagnosis.

7. A method according to claim 4 wherein electrical current is injected and withdrawn between successive pairs of points, and while current is being injected between each pair of points, a voltage measurement is taken between such pair of points.

8. A method according to claim 5, 6 or 7 wherein impedance values are determined from said respective pairs of points and the difference between said impedance values are analyzed for said diagnosis.

9. A method according to claim 5 wherein said points define a plurality of chords extending between respective pairs of points, said method including the step of graphically depicting the impedance measurements for each said first and second sets on two chord diagrams, and then analysing the two chord diagrams for said diagnosis.

10. A method according to claim 7 wherein said points define a plurality of chords extending between respective pairs of points, said method including the step of graphically depicting the impedance measurements for each said first and second sets on two chord diagrams, and then analysing the two chord diagrams for said diagnosis.

11. A method according to claim 9 or 10 in which chords of said diagrams that have impedances which are the same or within a selected difference from each other are removed, and then the remaining chords are compared for said diagnosis.

12. A method according to claim 2, wherein said points are arranged in a variety of geometrical patterns on each breast.

13. A method according to claim 2 wherein said points are arranged in a substantially circular pattern around a nipple of each of said breasts.

14. An electrode array for diagnosing the presence of a disease state in a living organism, said electrode array comprising a flexible backing material, and a plurality of pairs of electrodes spaced around said backing material, said electrodes being connected to terminals and being adapted to obtain impedance measurements between respective said electrodes.

15. An electrode array according to claim 14, wherein said electrodes include adhesive for fixation to the skin.

16. An electrode array according to claim 15 and including a positioning formation thereon to align and reproducibly position said electrode array over a selected part of said organism.

17. An electrode array according to claim 15 and including a separate positioning formation to align and reproducibly position said electrode array over a selected part of said organism.

18. A method of diagnosing the possibility of a disease state in one of first and second parts of a living organism, said parts being similar but having impedances which differ by consistent and known amounts, said method comprising:

(a) obtaining a plurality of impedance measurements across each of said parts and thereby producing first and second sets of impedance measurements, said first set for said first part, and said second set for said second part, (b) said measurements of said first set being taken across predetermined portions of said first part, and each measurement of said first set having a corresponding measurement in said second set taken across a corresponding portion of said second part, (c) comparing said sets to determine differences therebetween which are additional to said known amounts, and where there is a substantial difference other than said known amounts, diagnosing the possibility of a disease state.

19. A method according to claim 13 wherein said disease state is a cancer.

* * * * *